United States Patent
Okuda et al.

(10) Patent No.: US 9,259,182 B2
(45) Date of Patent: Feb. 16, 2016

(54) PORTABLE ELECTRONIC DEVICE

(71) Applicant: Seiko Instruments Inc., Chiba-shi, Chiba (JP)

(72) Inventors: Hideki Okuda, Chiba (JP); Dai Terasawa, Chiba (JP); Teruo Kato, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 14/518,510

(22) Filed: Oct. 20, 2014

(65) Prior Publication Data

US 2015/0119676 A1 Apr. 30, 2015

(30) Foreign Application Priority Data

Oct. 25, 2013 (JP) .................................. 2013-222410

(51) Int. Cl.
| | |
|---|---|
| *A61B 5/0408* | (2006.01) |
| *A61B 5/00* | (2006.01) |
| *A41D 1/00* | (2006.01) |
| *A41D 13/12* | (2006.01) |
| *A61B 5/024* | (2006.01) |
| *A61B 5/0245* | (2006.01) |

(52) U.S. Cl.
CPC .............. *A61B 5/6804* (2013.01); *A41D 1/002* (2013.01); *A41D 13/1281* (2013.01); *A61B 5/0006* (2013.01); *A61B 5/0245* (2013.01); *A61B 5/02438* (2013.01); *A61B 5/0408* (2013.01); *A61B 5/04085* (2013.01)

(58) Field of Classification Search
CPC . A61B 5/6804; A61B 5/6805; A61B 5/04085
USPC ....................................................... 600/388
See application file for complete search history.

(56) References Cited

U.S. PATENT DOCUMENTS

| | | | | |
|---|---|---|---|---|
| 5,610,877 | A * | 3/1997 | Adams et al. ................... | 368/10 |
| 7,124,447 | B2 * | 10/2006 | Arganese .......................... | 2/160 |
| 7,292,150 | B2 * | 11/2007 | Shaw ......................... | 340/573.1 |
| 7,793,361 | B2 * | 9/2010 | Ishihara et al. .................... | 2/170 |
| 8,663,106 | B2 * | 3/2014 | Stivoric et al. ................ | 600/301 |
| 8,897,852 | B2 * | 11/2014 | Kato ..................... | A61B 5/0408 |
| | | | | 600/390 |
| 2007/0073131 | A1 * | 3/2007 | Ryu et al. ...................... | 600/388 |
| 2007/0250981 | A1 * | 11/2007 | Seibert ................................ | 2/69 |
| 2010/0185398 | A1 * | 7/2010 | Berns ................ | A41D 13/1281 |
| | | | | 702/19 |

(Continued)

FOREIGN PATENT DOCUMENTS

| | | | |
|---|---|---|---|
| JP | 4721700 | B2 | 7/2011 |
| JP | 5176202 | B2 | 4/2013 |

*Primary Examiner* — Lee S Cohen
(74) *Attorney, Agent, or Firm* — Brinks Gilson & Lione

(57) ABSTRACT

To improve product lifetime as well as to increase wearing feeling, maintainability and productivity, and to suppress manufacturing costs and expenses of the user. A portable electronic device 10 includes a device body 20 arranged inside a garment W and housing an electronic component and a fixing member 30A formed separately from the device body 20 and arranged outside the garment W, which fixes the device body 20 so as to be attached and detached to and from the garment W in a state of sandwiching the garment W between the fixing member 30A and the device bogy 20 from the other side of the garment W. The fixing member 30A is formed so as to be elastically deformed, which is formed in a ring shape surrounding the device body 20. Gaps are provided on both sides of the device body 20 in the radial direction of the fixing member 30A between an inner peripheral surface of the fixing member 30A and the device body 20.

6 Claims, 12 Drawing Sheets

(56) References Cited

U.S. PATENT DOCUMENTS

| | | | |
|---|---|---|---|
| 2011/0166491 A1* | 7/2011 | Sankai | 601/84 |
| 2012/0165645 A1* | 6/2012 | Russell | A61B 5/0024 600/388 |
| 2012/0238910 A1* | 9/2012 | Nordstrom | 600/587 |
| 2013/0077263 A1* | 3/2013 | Oleson et al. | 361/747 |
| 2013/0204100 A1* | 8/2013 | Acquista | 600/301 |
| 2014/0259267 A1* | 9/2014 | Nordstrom | 2/69 |

* cited by examiner

PORTABLE ELECTRONIC DEVICE

RELATED APPLICATIONS

This application claims priority under 35 U.S.C. §119 to Japanese Patent Application No. 2013-222410 filed on Oct. 25, 2013, the entire content of which is hereby incorporated by reference.

BACKGROUND OF THE INVENTION

1. Field of the Invention

The present invention relates to a portable electronic device.

2. Description of the Related Art

There exist biological information detecting devices detecting a biological signal by attaching a sensor electrode to a biological surface. In this kind of biological information detecting devices, there is the one which measures a heart rate from the biological surface, for example, by detecting an electrocardiographic signal generated by heartbeats by the sensor electrode. As such a biological information detecting device, for example, there is the one which includes a sensor electrode and a device body (transmission unit) transmitting an electrocardiographic signal detected by the sensor electrode to the outside. The heart rate is measured by a separate receiving unit receiving the signal transmitted from the device body.

The sensor electrode and the device body are attached to a user's body by using a ring-shaped band having elasticity such as a rubber band. The user puts on the sensor electrode and the device body so that the ring-shaped band is attached around the body. Accordingly, the sensor electrode is pressed onto the biological surface and the electrocardiographic signal can be detected. It is necessary that the sensor electrode is held at a predetermined position in the body which is suitable for detecting the electrocardiographic signal during the use for positively detecting the electrocardiographic signal.

When the sensor electrode is held so as not to be displaced during exercise and so on, the user may feel a sense of oppression as a tightening force by the band is high.

In response to the above, a structure in which a band with a sensor electrode is integrally attached to a garment is disclosed in, for example, Japanese Patent No. 4721700 (Patent Literature 1).

Moreover, a structure in which a sensor electrode is woven into a garment as part of the garment by using conductive yarn is disclosed in, for example, Japanese Patent No. 5176202 (Patent Literature 2).

As shown in Patent Literatures 1 and 2, as the sensor electrode is integrally attached to the garment, a position of the sensor electrode with respect to the body is not largely displaced when the user wears the garment on the body.

However, in the structures disclosed in Patent Literatures 1 and 2, the sensor electrode is easily deteriorated by washing of the garment or the like as the sensor electrode is attached to the garment. Accordingly, there is room for improvement in extension of lifetime of the biological information detecting device.

The position of the sensor electrode is determined by a position where the sensor band is woven into the garment. Therefore, the sensor electrode is not always arranged in an appropriate position with respect to the body in the state where the garment is worn on the body due to the individual difference even when the user selects the garment in the appropriate size for the user's body. Additionally, as the sensor electrode is previously provided in the garment, it is difficult to adjust the position of the sensor electrode so as to correspond to the user, therefore, the degree of freedom in the attachment position is low. Therefore, there is a danger that detection performance in the sensor electrode is reduced when the position of the sensor electrode is inappropriate. The position of the sensor electrode may give uncomfortable feeling to the user in the state where the user puts on the sensor, which may cause a problem in wearing feeling.

It can be considered that other various electronic devices such as a music player are attached to the garment in the same manner, not limited to the biological information detecting device. Also in this case, the above-described problems exist in common.

SUMMARY OF THE INVENTION

In view of the above, an object of the present invention is to provide a portable electronic device capable of improving product lifetime as well as being attached to an arbitrary position.

According to an embodiment of the invention, there is provided a portable electronic device including a device body arranged in one side of the front side and the reverse side of a garment and housing an electronic component and a fixing member formed separately from the device body and arranged in the other side of the front side and the reverse side of the garment, which fixes the device body so as to be attached and detached to and from the garment in a state of sandwiching the garment between the fixing member and the device body from the other side of the front side and the reverse side of the garment.

According to the present invention, the device body can be fixed by the fixing member so as to be attached and detached at an arbitrary position of the garment. Accordingly, the user can attach the device body so as to be fitted to a body of himself/herself, therefore, the device can be attached to an arbitrary position to thereby carry out given functions. It is also possible to attach the device body at a position comfortable for the user.

Moreover, when the fixing of the device body by the fixing member is released, the device body and the fixing member can be detached from the garment, and only the garment can be washed. Therefore, the garment can be changed freely and the device body is not deteriorated by the washing, which improves product lifetime.

The fixing member may fix an outer peripheral portion of the device body at least at two places.

According to the present invention, the device body can be fixed easily without piercing the garment with the fixing member.

The device body may include a locked portion to which the fixing member is locked, and the fixing member may be formed so as to be elastically deformed, including a locking portion which can be locked to the locked portion.

According to the present invention, the locking portion of the fixing member can be easily locked to the locked portion of the device body, thereby fixing the device body positively.

The fixing member may be formed in a ring shape surrounding the device body.

According to the present invention, the fixing member can be manufactured at low costs as the fixing member has a simple shape.

A gap may be provided at least in one side of the device body in a radial direction of the fixing member between an inner peripheral surface of the fixing member and the device body.

According to the present invention, it is possible to elastically deform the fixing member and to release the fixing of the device body by the fixing member by pressing a position corresponding to the gap provided between the inner peripheral surface of the fixing member and the device body in the outer peripheral surface of the fixing member. Therefore, the device body can be detached from the garment easily.

The fixing member may include a protective portion covering at least part of the device body through the garment from the other side of the front side and the reverse side of the garment.

According to the present invention, it is possible to prevent the damage and so on in the device body and the garment where the device body is attached by the fixing member.

The portable electronic device may further include the device body, a pair of electrode portions connected to the device body and contacting a biological surface and a biological information detecting unit detecting biological information based on a potential difference generated in the pair of electrode portions.

According to the present invention, a biological signal can be detected from the biological surface by the pair of electrode portions. As it is not necessary to weave the electrodes into the garment, deterioration of the electrodes caused by the washing or the like can be prevented as well as detection performance can be stabilized.

According to the invention, the device body can be fixed at an arbitrary position of the garment so as to be attached/detached by the fixing member. Accordingly, the user can attach the device body so as to be fitted to the body of himself/herself, therefore, the device body can be attached to an arbitrary position to thereby carry out given functions. It is also possible to attach the device body at a position comfortable for the user.

Moreover, when the fixing of the device body by the fixing member is released, the device body and the fixing member can be detached from the garment, and only the garment can be washed. Therefore, the garment can be changed freely and the device body is not deteriorated by the washing, which improves product lifetime.

BRIEF DESCRIPTION OF THE DRAWINGS

FIGS. 7(a) and 7(b) are views showing a state where the heart rate measuring device is attached to the garment, in which FIG. 7(a) is a front view and FIG. 7(b) is a transverse sectional view.

FIGS. 8(a) and 8(b) are views showing a state where the heart rate measuring device is detached from the garment, in which FIG. 8(a) is a front view and FIG. 8(b) is a transverse sectional view.

DETAILED DESCRIPTION OF THE PREFERRED EMBODIMENTS

First Embodiment

Next, a first embodiment of the present invention will be explained with reference to the drawings.

Figure 1:
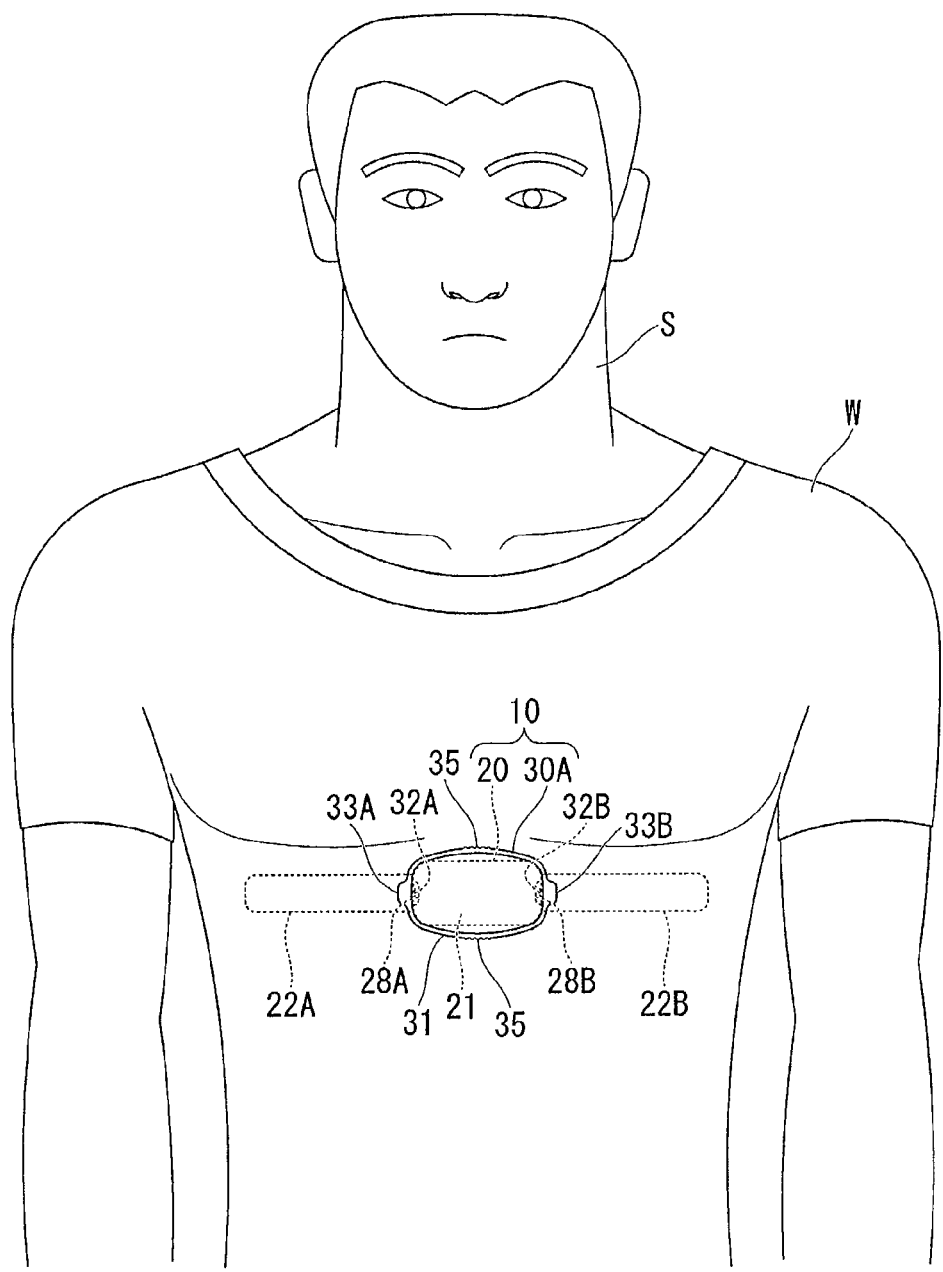
FIG. 1 is a front view showing a state where a heart rate measuring device as a portable electronic device according to a first embodiment of the present invention is attached to a user.
Figure 2:
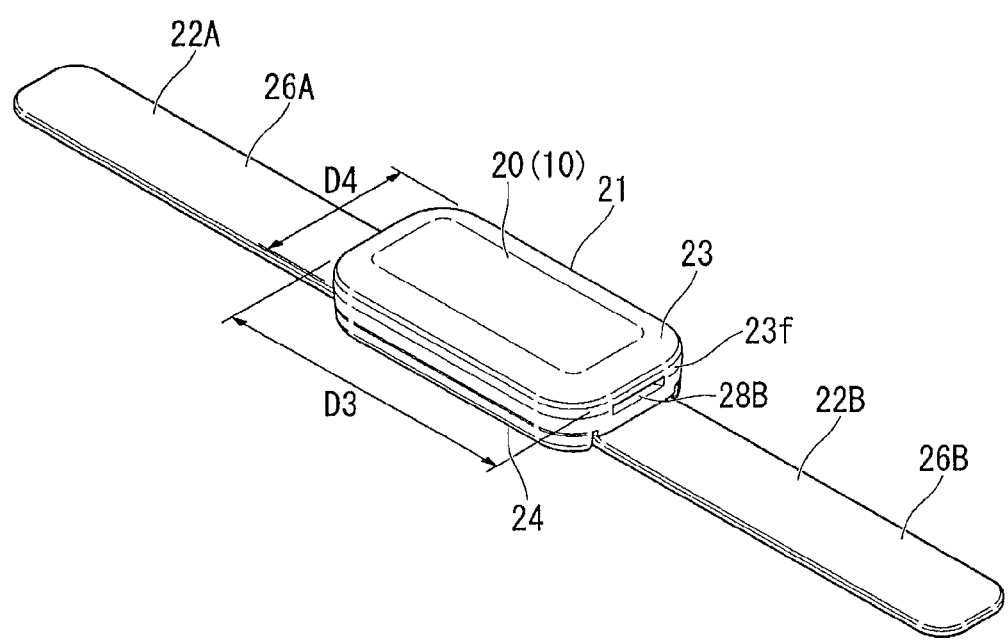
FIG. 2 is a perspective view of the device body included in the heart rate measuring device.

FIG. 1 is a front view showing a state where a heart rate measuring device as a portable electronic device according to the present invention is attached to a user, and FIG. 2 is a perspective view showing a device body included in the heart rate measuring device.

As shown in FIG. 1, a heart rate measuring device (corresponding to a "portable electronic device" in claims) 10 detects an electrocardiographic signal generated by heartbeats by being attached to a chest as a biological surface of a user S, and transmits the detected electrocardiographic signal by wireless communication.

The heart rate measuring device 10 includes a device body 20 and a fixing member 30A for attaching the device body 20 to a garment W worn by the user S.

As shown in FIG. 1 and FIG. 2, the device body 20 includes a case 21 formed in a rectangular shape in planar view, a not-shown detection circuit substrate (corresponding to a "biological information detecting unit" in claims) provided in the case 21 and a pair of heart rate detecting portions 22A and 22B integrally formed on both sides of the case 21.

Figure 3:
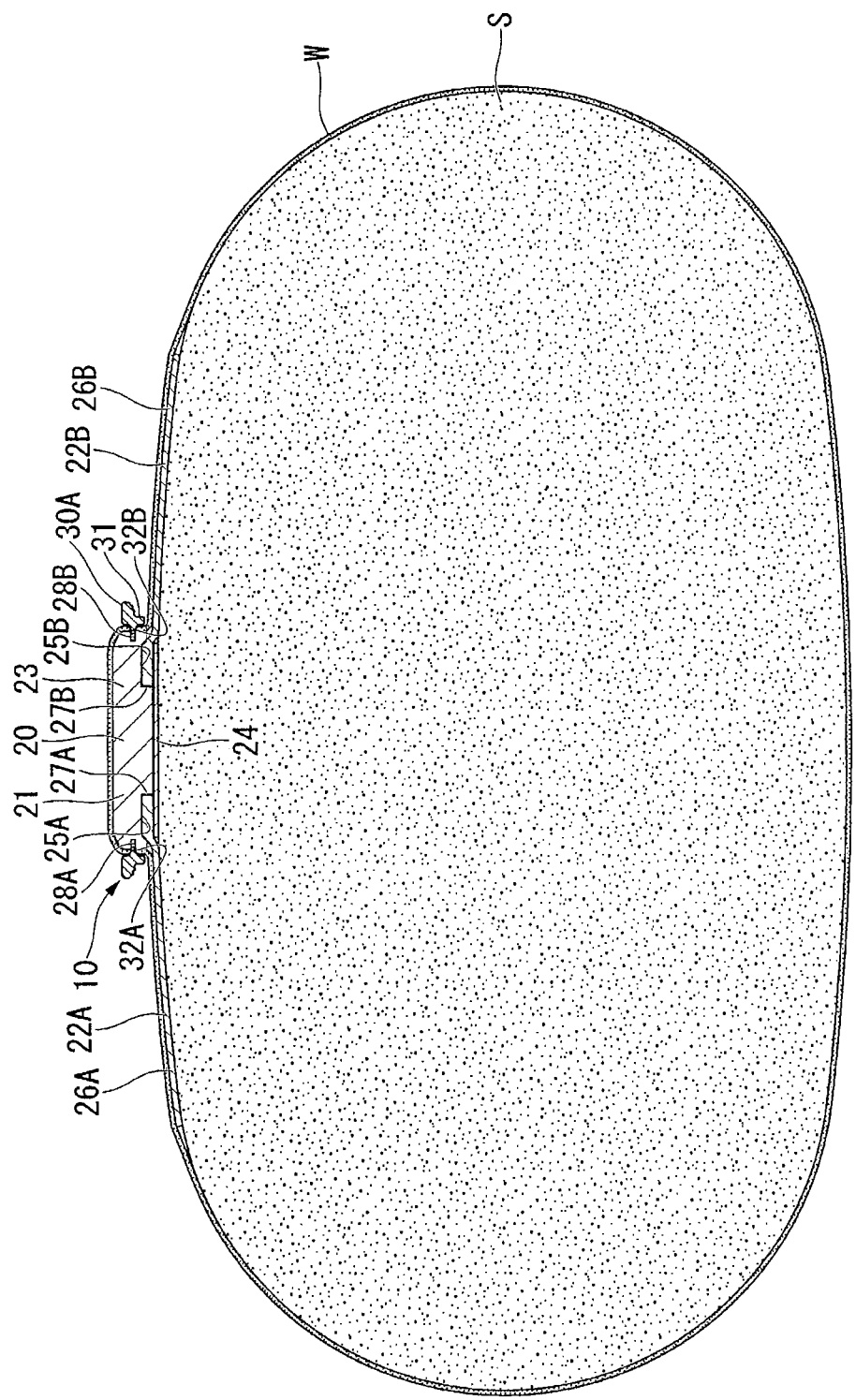
FIG. 3 is a transverse sectional view showing a state where the heart rate measuring device is attached to a user.
Figure 4:
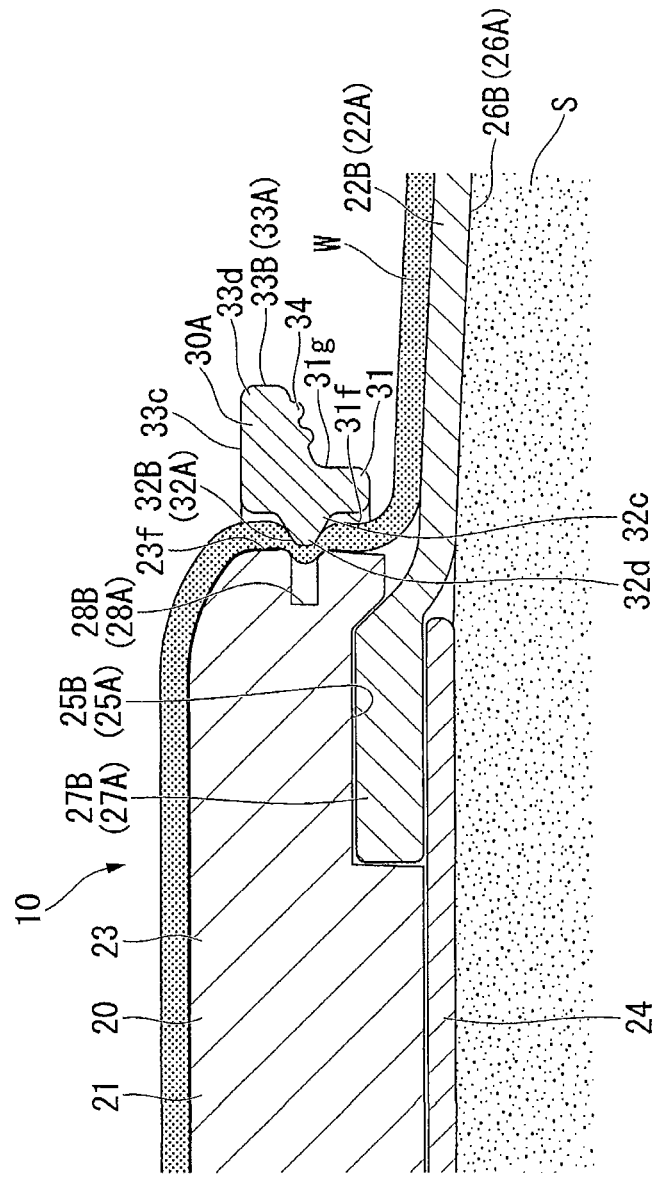
FIG. 4 is an enlarged view of a relevant part of FIG. 3.

FIG. 3 is a transverse sectional view showing a state where the heart rate measuring device is attached to the user, and FIG. 4 is an enlarged view of a relevant part of FIG. 3.

As shown in FIG. 3 and FIG. 4, the case 21 includes a case body 23 accommodating the not-shown detection circuit substrate and a back plate 24 attached to one surface side of the case body 23. In the case body 23, holding concave portions 25A and 25B for holding base end portions of the heart rate detecting portions 22A and 22B are formed on both end portions in the longitudinal direction of the case body having the rectangular shape on the side opposite to the back plate 24.

In an outer peripheral end surface 23f of the case body 23, concave portions 28A and 28B (corresponding to a "locked portion" in claims) which are concave toward the inside of the case body 23 are formed at least at two places which are opposite to each other with respect to the center of the case body 23 as locked portions to which the fixing member 30A is locked.

The detection circuit substrate includes a transmission circuit generating an electric signal based on a signal detected by the pair of heart rate detecting portions 22A and 22B and a wireless transmission portion (both are not shown) transmitting the electric signal generated in the transmission circuit to the outside.

The heart rate detecting portions 22A and 22B are respectively formed by band-shaped electrodes (corresponding to "electrode portions" in claims) 26A and 26B which are made of conductive elastomer. As the conductive elastomer, for example, conductive silicon rubber in which carbon black is blended, conductive rubber in which carbon black is blended, conductive polyurethane rubber in which carbon black is blended and so on can be used.

The respective heart rate detecting portions 22A and 22B are arranged in both sides interposing the device body 20 therebetween. The respective heart rate detecting portions 22A and 22B are sandwiched between the back plate 24 and the base body 23 to be mechanically connected in a state where connecting portions 27A and 27B each formed in one side in the longitudinal direction are accommodated inside the holding concave portions 25A and 25B of the case body 23. The electrodes 26A and 26B are electrically connected to the detection circuit substrate inside the holding concave portions 25A and 25B.

Accordingly, the signal detected by the electrodes 26A and 26B is outputted to the detection circuit substrate.

In the above device body 20, an electrocardiographic signal generated by heartbeats is detected by the pair of electrodes 26A and 26B. The not-shown detection circuit substrate of the device body 20 outputs the electrocardiographic signal detected by the pair of electrodes 26A and 26B to the outside.

Figure 5:
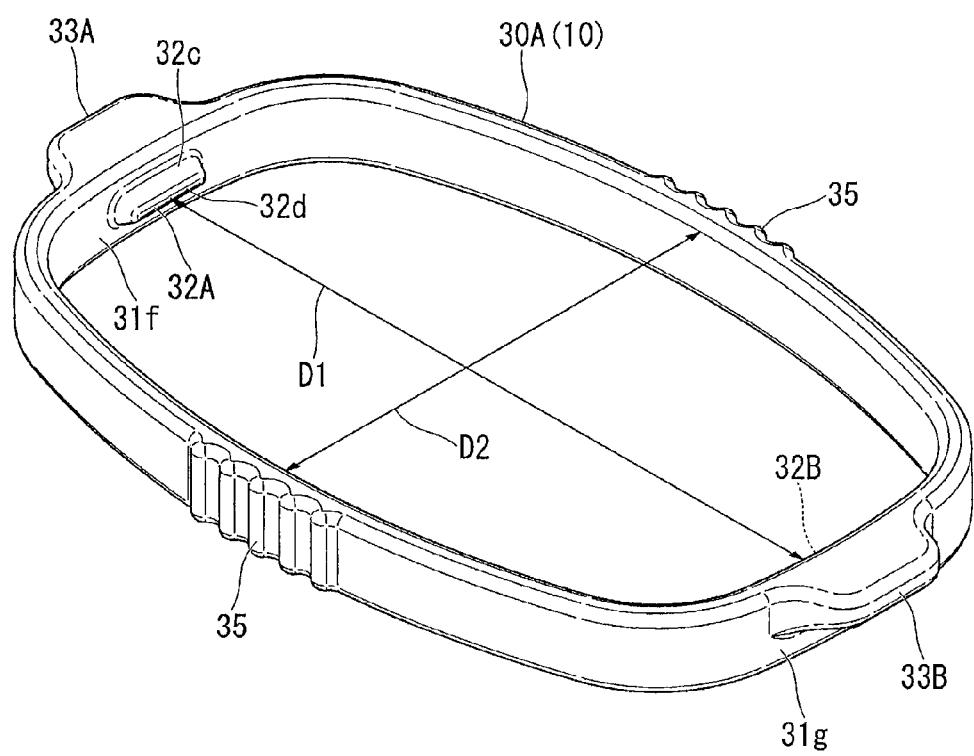
FIG. 5 is a perspective view showing a fixing member included in the heart rate measuring device.

FIG. 5 is a perspective view of the fixing member included in the heart rate measuring device.

As shown in FIG. 4 and FIG. 5, the fixing member 30A includes a ring-shaped portion 31 having an oval shape in planar view formed in a ring shape surrounding the device body 20, and locking portions 32A and 32B formed at two places in a circumferential direction of the ring-shaped portion 31.

The ring-shaped portion 31 has an approximately oval shape as a whole so as to be arranged along the outer peripheral end surface 23f of the case body 23 forming the device body 20. The ring-shaped portion 31 is made of materials which can be elastically deformed such as rubber materials, soft resin materials and metal materials.

As shown in FIG. 5, the ring-shaped portion 31 is formed so that a separation distance D1 between the locking portions 32A and 32B extending along the long-axis direction is smaller than an outer diameter distance D3 (see FIG. 2) in the longitudinal direction of the case body 23 and so that an inner diameter distance D2 in the short-axis direction is larger than an outer diameter distance D4 (see FIG. 2) in the short length direction of the case body 23 in a state where the fixing means 30A is not attached to the device body 20.

The locking portions 32A and 32B are formed so as to be opposite to each other in the long-axis direction in an inner peripheral surface 31f of the ring-shaped portion 31. As sown in FIG. 4, the locking portions 32A and 32B are respectively formed so as to protrude inward from the inner peripheral surface 31f of the ring-shaped portion 31, and so that the size in a thickness direction of the ring-shaped portion 31 is gradually reduced from a base end 32c toward a tip portion 32d in the inner peripheral surface 31f side. The locking portions 32A and 32B can be locked to the concave portions 28A and 28B formed in the outer peripheral end surface 23f of the case body 23.

Also, in an outer peripheral surface 31g of the ring-shaped portion 31, protrusions 33A and 33B protruding toward the outer peripheral side are formed at positions where the locking portions 32A and 32B are formed. The protrusions 33A and 33B are formed so that the size in the thickness direction of the ring-shaped portion 31 is gradually reduced from a base end portion 33c toward a tip portion 33d in the outer peripheral surface 31g side of the ring-shaped portion 31. Also in the protrusions 33A and 33B, projections and depressions 34 as slip stoppers are formed in surfaces facing one side (user S's side in the embodiment) of the ring-shaped portion 31.

As shown in FIG. 5, projections and depressions 35 as slip stoppers are also formed in both end portions in the short-axis direction on the outer peripheral surface 31g of the ring-shaped portion 31.

Figure 6:
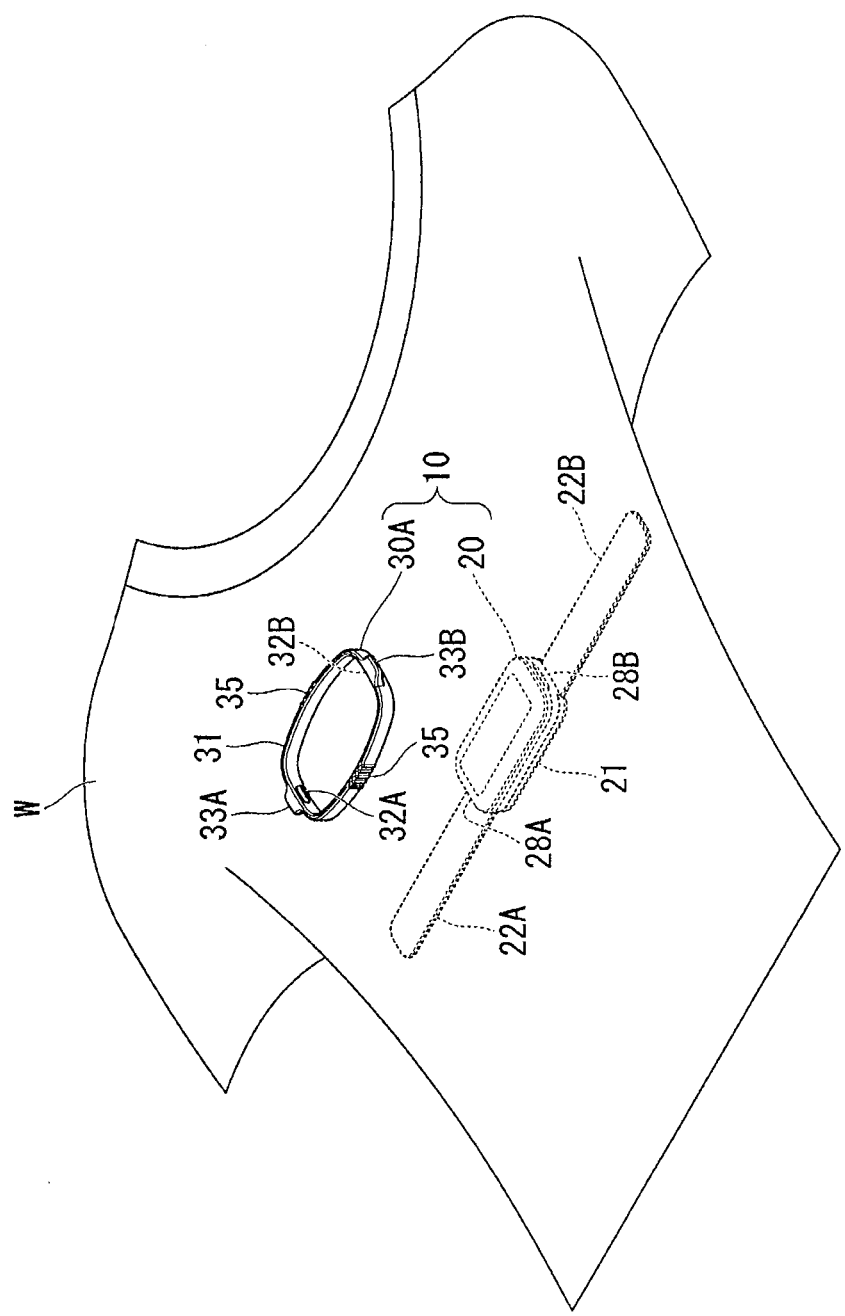
FIG. 6 is a perspective view showing the fixing member and the device body with respect to a garment at the time of attaching the heart rate measuring device to the garment.
Figure 7A:
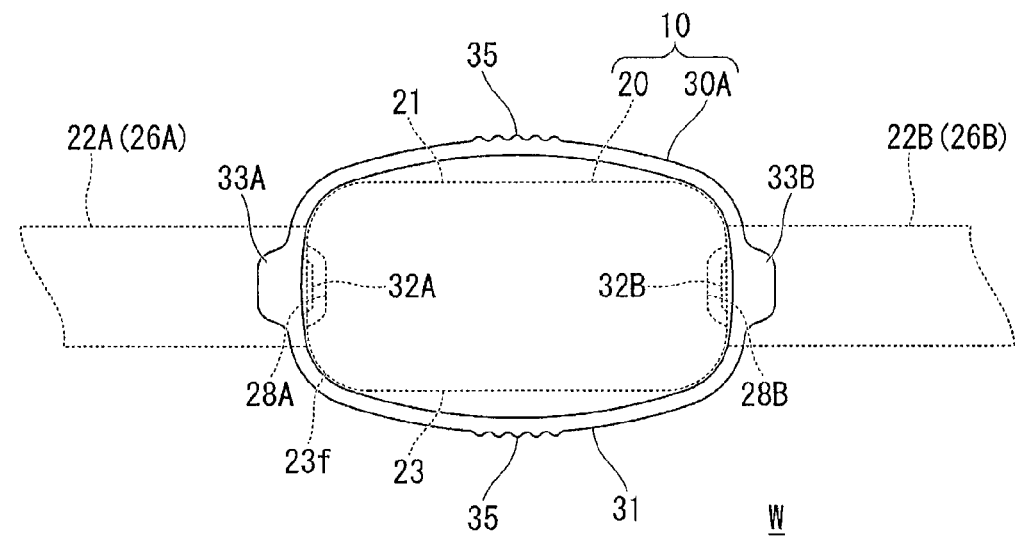
Figure 7B:
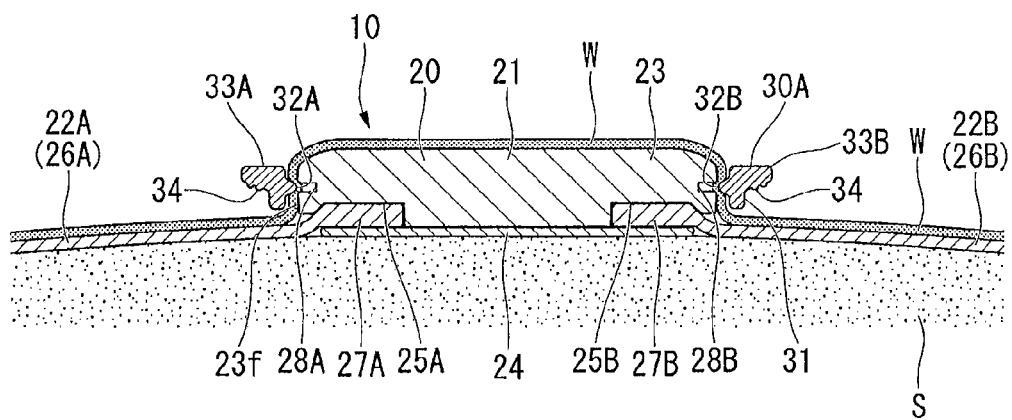

FIG. 6 is a perspective view showing an arrangement of the fixing member and the device body with respect to the garment at the time of attaching the heart rate measuring device to the garment. FIGS. 7(a) and 7(b) are views showing a state where the heart rate measuring device is attached to the garment, in which FIG. 7(a) is a front view and FIG. 7(b) is a transverse sectional view.

As shown in FIG. 6, the above-described heart rate measuring device 10 is used in a state of being attached to the garment W. The device body 20 is arranged inside the garment W (in the body side of the user S). The fixing member 30A is arranged outside the garment W, which is the opposite side (the other side) of the side where the device body 20 is arranged.

Then, the fixing member 30A is fitted to the outer peripheral portion of the device body 20 in a state of sandwiching the garment W between the fixing member 30A and the device body 20 from the other side of the garment W as shown in FIGS. 3, 4, 7(a) and 7(b). Accordingly, the device body 20 is fixed to the garment W by the fixing member 30A so as to be attached/detached. The garment W is sandwiched between the outer peripheral end surface 23f of the case body 23 and the fixing member 30A so as to abut along the outer peripheral surface of the device body 20 in the above state.

The locking portions 32A and 32B of the fixing member 30A are locked to the concave portions 28A and 28B of the device body 20. When the locking portions 32A and 32B are locked to the concave portions 28A and 28B, the locking portions 32A and 32B of the ring-shaped portion 31 follow the outer peripheral end surface 23f of the case body 23, thereby allowing the ring-shaped portion 31 to be elastically deformed in a direction of expanding the diameter in the long-axis direction. Then, the locking portions 32A and 32B move along the outer peripheral end surface 23f of the case body 23 and are fitted to the concave portions 28A and 28B to be locked. At this time, as the separation distance D1 between the locking portions 32A and 32B of the fixing member 30A is smaller than the outer diameter distance D3 in the longitudinal direction of the case body 23, the locking portions 32A and 32B enter the concave portions 28A and 28B to thereby maintain the locked state. According to the structure, the fixing means 30A is not easily separated from the device body 20.

In this case, the ring-shaped portion 31 is formed so that the inner diameter distance D2 (see FIG. 5) in the short-axis direction is larger than the outer diameter distance D4 (see FIG. 2) in the short length direction of the case body 23. Therefore, gaps are formed on both sides of the device body 20 in the short-axis direction of the fixing member 30A between the inner peripheral surface 31f of the fixing member 30A and the device body 20.

Figure 8A:
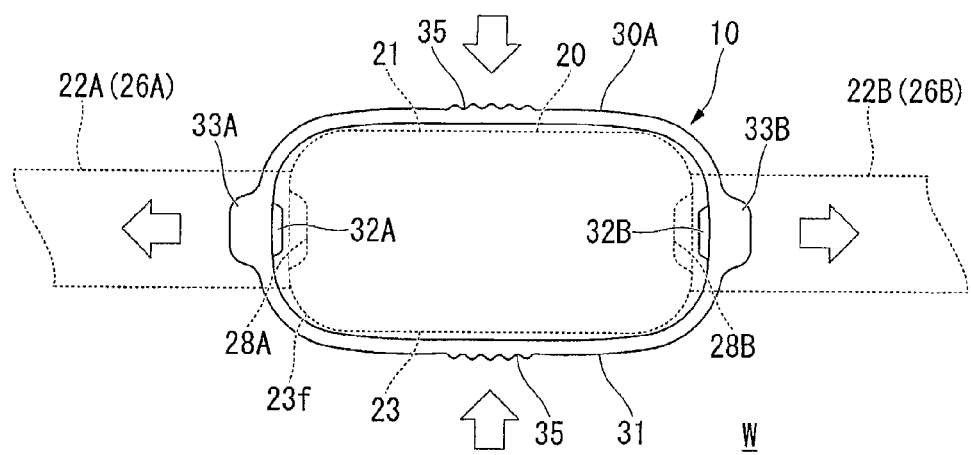
Figure 8B:
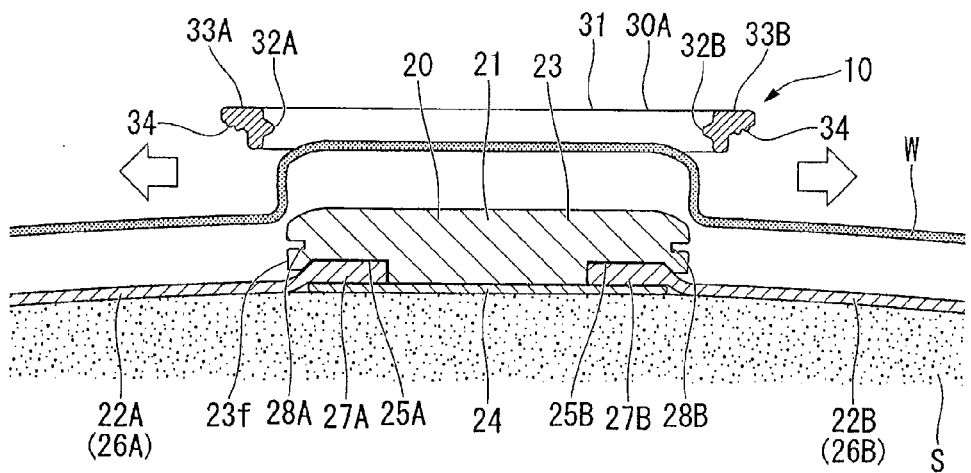

FIGS. 8(a) and 8(b) are views showing a state where the heart rate measuring device is detached from the garment, in which FIG. 8(a) is a front view and FIG. 8(b) is a transverse sectional view.

As shown in FIGS. 8(a) and 8(b), the ring-shaped portion 31 is pressed at portions of the projections and depressions 35, 35 toward the inside of the short-axis direction at the time of detaching the fixing member 30A from the device body 20. Then, the inner diameter in the short-axis direction of the ring-shaped portion 31 is reduced, therefore, the fixing member 30A is elastically deformed so that the outer diameter in the long-axis direction is increased. Accordingly, the locking portions 32A and 32B are separated from the concave portions 28A and 28B, thereby releasing the lock. Sequentially, the protrusions 33A and 33B are picked by fingers so that the protrusions 33A and 33B are moved in a direction in which the fixing member 30A is detached from the surface of the garment W. Accordingly, the fixing member 30A is detached from the outer peripheral portion of the device body 20, and the positioning between the device body 20 and the fixing member 30A with respect to the garment W is released.

When the fixing member 30A is detached from the device body 20, it is also preferable that the locking portions 32A and 32B are separated from the concave portions 28A and 28B by picking the protrusions 33A and 33B by fingers and pulling the protrusions 33A and 33B in a direction in which the protrusions 33A and 33B move away from each other (the long-axis direction of the fixing member 30A).

Here, the garment W is preferably a so-called compression wear formed by a stretch material having elasticity and supporting muscle by wrapping the body moderately. That is because the heart rate detecting portions 22A and 22B of the device body 20 can closely contact the surface of the body of the user S and the detection of the biological signal can be performed with high sensitivity.

The above-described heart rate measuring device 10 includes the device body 20 which is arranged in the inside (reverse side) of the garment W and houses an electronic component and the fixing member 30A formed separately from the device body 20 and arranged in the outside (front side) of the garment W, which fixes the device body 20 to the garment W so as to be attached/detached in the state of sandwiching the garment W between the fixing member 30A and the device body 20 from the outside of the garment W.

According to the structure, the device body 20 can be fixed at an arbitrary position of the garment W so as to be attached/detached by the fixing member 30A.

Therefore, the device body 20 can be attached so as to be fitted to the body of the user S. As a result, it is possible to attach the device body 20 at an arbitrary position to thereby carry out given functions. It is also possible to attach the device body 20 at a position comfortable for the user S.

Moreover, when the garment W is washed, the device body 20 and the fixing member 30A can be detached from the garment W by releasing the fixing of the device body 20 by the fixing member 30A. Therefore, it is possible to change the garment W freely and there is no difficulty in washing and so on.

Accordingly, it is possible to prevent the degradation of wearing feeling of the garment W due to the attachment of the heart rate measuring device 10. Additionally, as the heart rate measuring device 10 is provided separately from the garment W, maintainability and productivity can be increased as well as manufacturing costs can be suppressed. Even when the user S uses the heart rate measuring device 10 day after day, the heart rate measuring device 10 can be attached to each of plural garments W one after another. Accordingly, as just one heart rate measuring device 10 is required, expenses can be suppressed.

The fixing member 30A fixes the outer peripheral portion of the device body 20 at least at two places with an interval in the circumferential direction of the device body 20.

According to the above structure, the device body 20 can be fixed without piercing the garment W with the fixing member 30A.

Furthermore, the device body 20 has the concave portions 28A and 28B to which the fixing member 30A is locked, and the fixing member 30A can be elastically deformed and has the locking portions 32A and 32B to be locked to the concave portions 28A and 28B.

According to the above structure, the fixing member 30A is elastically deformed and the locking portions 32A and 32B of the fixing member 30A are locked to the concave portions 28A and 28B of the device body 20, thereby fixing the device body 20 easily and stably.

The fixing member 30A is formed in a ring shape which surrounds the device body 20.

According to the above structure, the fixing member 30A can be manufactured at low costs as the fixing member 30A has a simple shape.

A pair of gaps are provided on both sides of the device body 20 in the short-axis direction of the fixing member 30A between the inner peripheral surface 31f of the fixing member 30A and the device body 20.

According to the above, the projections and depressions 35 corresponding to the gaps provided between the inner peripheral surface 31f of the fixing member 30A and the device body 20 in the outer peripheral surface 31g of the fixing member 30A are pressed, thereby elastically deforming the fixing member 30A as well as releasing the fixing of the device body 20 by the fixing member 30A. Therefore, the device body 20 can be detached from the garment W easily.

Furthermore, the device body 20 includes the pair of electrodes 26A and 26B which contact the body of the user S.

According to the above structure, a biological signal can be detected from the user S by the pair of electrodes 26A and 26B. Accordingly, it is not necessary to weave the electrodes 26A and 26B into the garment W. Therefore, the deterioration of electrodes by the washing does not occur, thereby stabilizing the detection performance.

Second Embodiment

Figure 9:
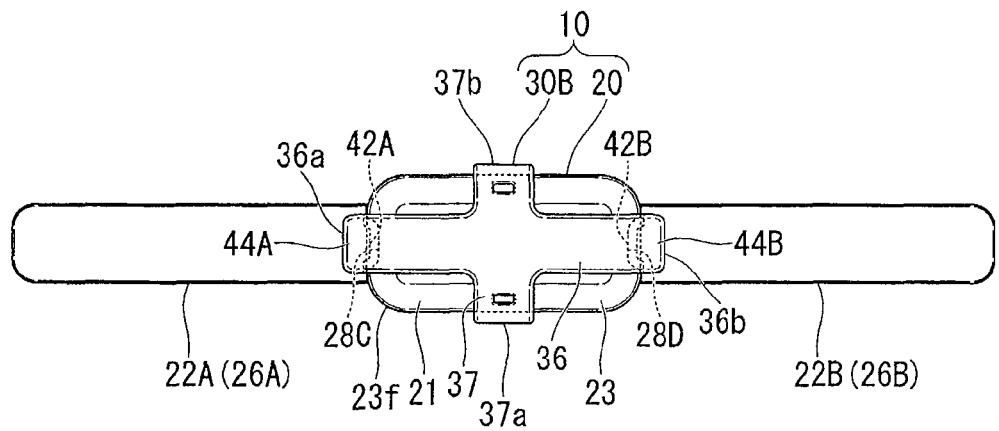
FIG. 9 is a front view showing a heart rate measuring device as a portable electronic device according to a second embodiment of the present invention.
Figure 10:
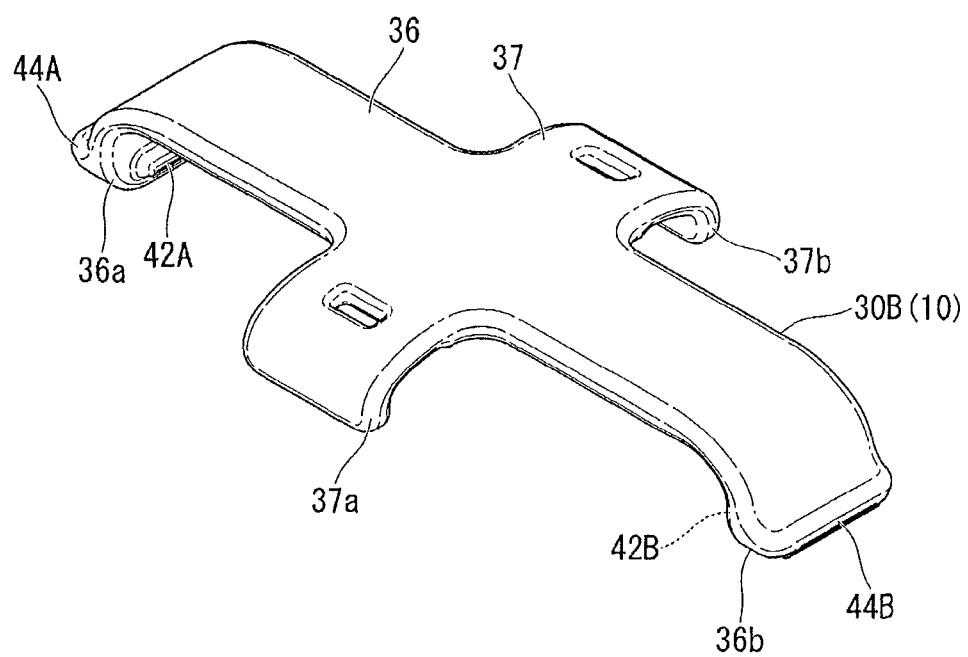
FIG. 10 is a perspective view of a fixing member included in the heart rate measuring device.

FIG. 9 is a front view showing a heart rage measuring device as a portable electronic device according to a second embodiment of the present invention. FIG. 10 is a perspective view of a fixing member included in the heart rate measuring device.

Next, the portable electronic device according to the second embodiment of the present invention will be explained.

In the first embodiment, the fixing member 30A is formed in the ring shape (see FIG. 1).

Whereas, the second embodiment differs from the first embodiment in a point that a fixing member 30B is formed to have a cross shape in a front view as shown in FIG. 9. In the second embodiment described below, the components common to the first embodiment are denoted by the same reference numerals and signs in the drawing, and the explanation thereof is omitted.

As shown in FIG. 9 and FIG. 10, the heart rate measuring device 10 includes the device body 20 having the same structure as the first embodiment and the fixing member 30B for attaching the device body 20 to the garment W to be worn by the user S.

In the outer peripheral end surface 23f of the case body 23 included in the device body 20, concave portions 28C and 28D which are concave toward the inside of the case body 23 are formed at least at two places which are opposite to each other with respect to the center of the case body 23, that is, at two places of both end portions in the longitudinal direction of the case body 23 in this embodiment, as locked portions to which the fixing member 30B is locked.

The fixing member 30B has a cross shape, including a first band-shaped portion (corresponding to a "protective portion" in claims) 36 extending in one direction and a second band-shaped portion (corresponding to a "protective portion" in claims) 37 which is orthogonal to the first band-shaped portion 36 at an intermediate portion in the longitudinal direction of the first band-shaped portion 36. The first band-shaped portion 36 and the second band-shaped portion 37 are formed so that the first band-shaped portion 36 extends along the longitudinal direction of the device body 20 and the second band-shaped portion 37 extends along the short length direction of the device body 20 in the state where the fixing member 30B is attached to the device body 20.

Both end portions 36a and 36b of the first band-shaped portion 36 and both end portions 37a and 37b of the second band-shaped portion 37 are curved toward one side with respect to a surface where the first band-shaped portion 36 and the second band-shaped portion 37 are positioned. In tip portions of the both end portions 36a and 36b of the first band-shaped portion 36, locking protrusions (corresponding to a "locking portion" in claims) 42A and 42B respectively protruding toward the inside of the curved direction (center side of the fixing member 30B) are formed. Moreover, in tip portions of the both end portions 36a and 36b of the first band-shaped portion 36, protrusions 44A and 44B respectively protruding toward the outside of the curved direction are formed. The protrusions 44A and 44B are formed so that the thickness thereof is gradually reduced from base end portions toward tip end portions.

The above-described heart rate measuring device 10 is used in a state of being attached to the garment W worn by the user S. The device body 20 is disposed inside the garment W (in the body side of the user S). The fixing member 30B is arranged outside the garment W, which is the opposite side (the other side) of the side where the device body 20 is arranged.

Then, the fixing member 30B is fitted to the outer peripheral portion of the device body 20 in a state of sandwiching the garment W between the fixing member 30B and the device body 20 from the outer side of the garment W. Accordingly, the device body 20 is fixed to the garment W by the fixing member 30B so as to be attached/detached. The garment W is sandwiched between the case body 23 and the first band-shaped portion 36 as well as the second band-shaped portion 37 of the fixing member 30B so as to abut along the outer peripheral surface of the device body 20 in the above state.

The locking protrusions 42A and 42B formed in the both end portions 36a and 36b of the first band-shaped portion 36 are locked to the concave portions 28C and 28D of the device body 20. When the locking protrusions 42A and 42B are locked to the concave portions 28C and 28D, locking protrusions 42A and 42B follow the outer peripheral end surface 23f of the case body 23, thereby allowing the first band-shaped portion 36 to be elastically deformed. Then, the locking protrusions 42A and 42B move along the outer peripheral end surface 23f of the case body 23 and are fitted to the concave portions 28C and 28C to be locked.

In the fixing member 30B, the first band-shaped portion 36 and the second band-shaped portion 37 cover a side facing the outer side of the device body 20 and the garment W. Accordingly, the device body 20 and the garment W are protected.

When the fixing member 30B is detached from the device body 20, the fixing member 30B is pulled up by putting fingers in the protrusions 44A and 44B formed in the both end portions 36a and 36b of the first band-shaped portion 36. Then, the first band-shaped portion 36 is elastically deformed, the both end portions 36a and 36b are separated from the case body 23 and the protrusions 44A and 44B are removed from the concave portions 28C and 28D, thereby releasing the lock. Accordingly, the fixing member 30B is detached from the outer peripheral portion of the device body 20, and the positioning between the device body 20 and the fixing means 30B with respect to the garment W is released.

Also in the above-described heart rate measuring device 10 according to the second embodiment, in the same manner as the first embodiment, it is possible to prevent the degradation of wearing feeling of the garment W due to the attachment of the heart rate measuring device 10. Additionally, as the heart rate measuring device 10 is provided separately from the garment W, maintainability and productivity can be increased as well as manufacturing costs can be suppressed. Additionally, just one heart rate measuring device 10 is required for the user S, therefore, expenses can be suppressed.

Also, in the fixing member 30B, the first band-shaped portion 36 and the second band-shaped portion 37 cover part of the side facing the outer side of the device body 20 and the garment W. Accordingly, the device body 20 and the garment W are protected and it is possible to prevent the damage of the device body 20 and the garment W.

First Modification Example of Second Embodiment

Next, respective modification examples of the second embodiment will be described. In the above second embodiment, the fixing member 30B is formed so that the first band-shaped portion 36 and the second band-shaped portion 37 make the cross shape, however, the present invention is not limited to this.

Figure 11:
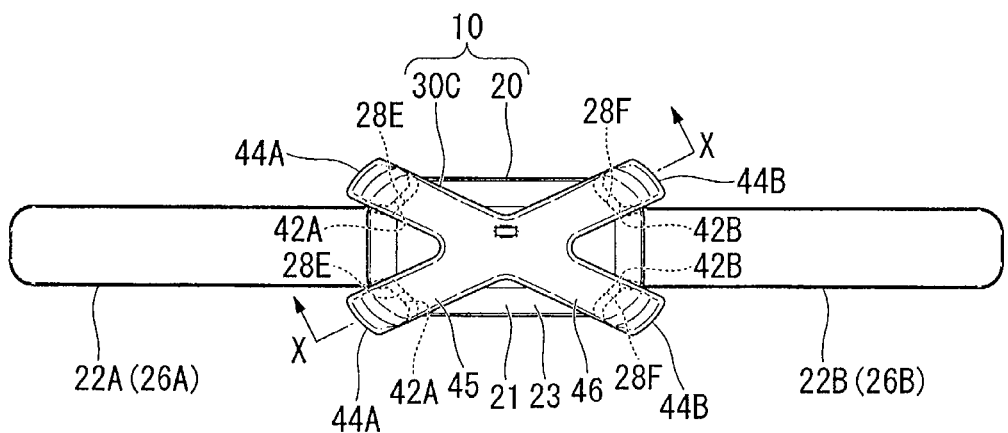
FIG. 11 is a front view showing a heart rate measuring device according to a modification example of the second embodiment of the present invention.
Figure 12:
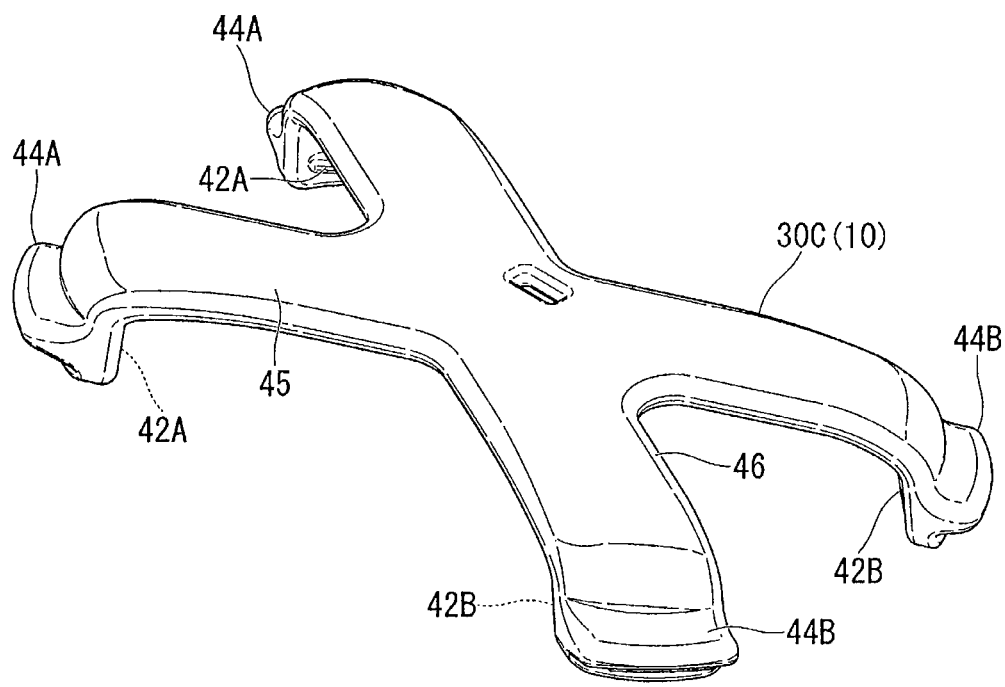
FIG. 12 is a perspective view of a fixing member included in the heart rate measuring device.
Figure 13:
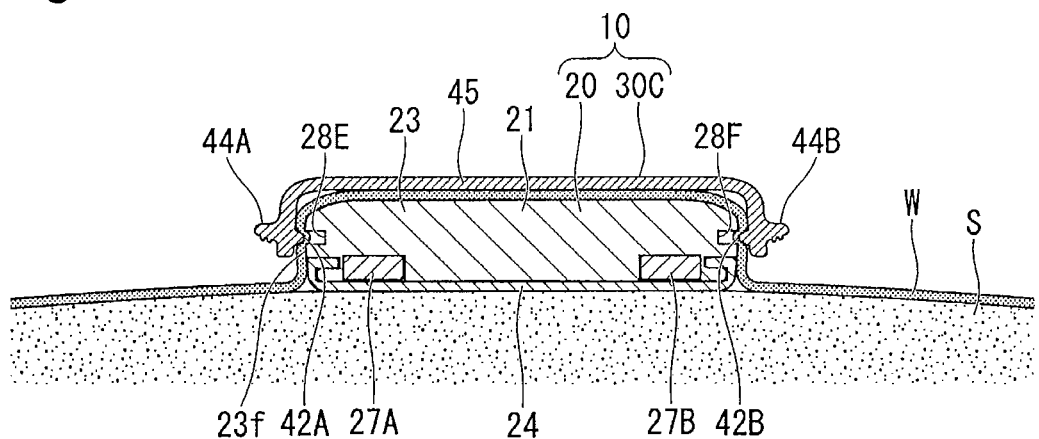
FIG. 13 is a cross-sectional view taken along X-X line of FIG. 11.

FIG. 11 is a front view showing a heart rate measuring device as a first modification example of the second embodiment of the present invention. FIG. 12 is a perspective view of a fixing member included in the heart rate measuring device. FIG. 13 is a cross-sectional view taken along X-X line of FIG. 11.

For example, as shown in FIG. 11 to FIG. 13, a fixing member 30C has an X-shape in a state of being attached to the device body 20, including a first band-shaped portion (corresponding to a "protective portion" in claims) 45 and a second band-shaped portion (protective portion) 46 which extend in diagonal directions of the device body 20.

Then, both end portions of the first band-shaped portion 45 and the second band-shaped portion 46 are curved toward one side with respect to a surface where the first band-shaped portion 45 and the second band-shaped portion 46 are positioned so as to extend along the case body 23. In both end portions of the first band-shaped portion 45 and the second band-shaped portion 46, the locking protrusions 42A and 42B, and the protrusions 44A and 44B are respectively formed.

In the device body 20 side to be fixed to the garment W by the above fixing member 30C, concave portions 28E and 28F which are concave toward the inside of the case body 23 are formed at positions corresponding to the locking protrusions 42A and 42B as locked portions to which the locking protrusions 42A and 42B of the fixing member 30C are locked.

Second Modification Example of Second Embodiment

Figure 14:
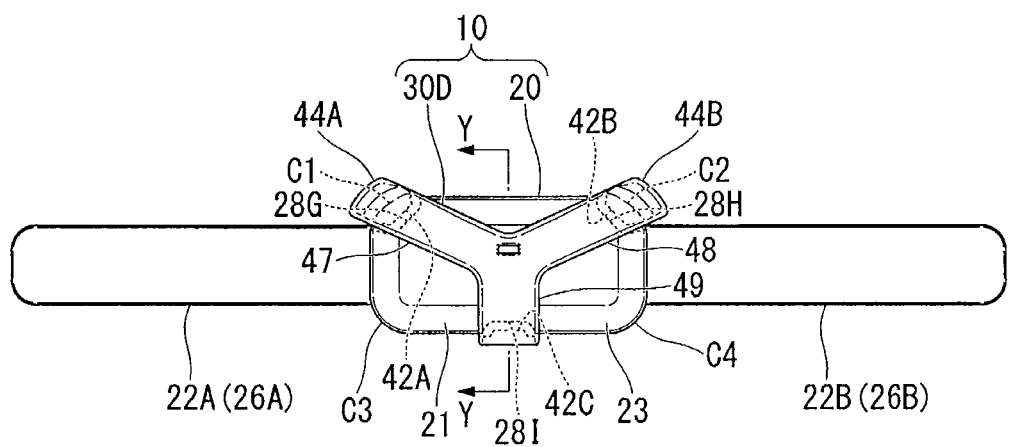
FIG. 14 is a front view showing a heart rate measuring device according to a modification example of the second embodiment of the present invention.
Figure 15:
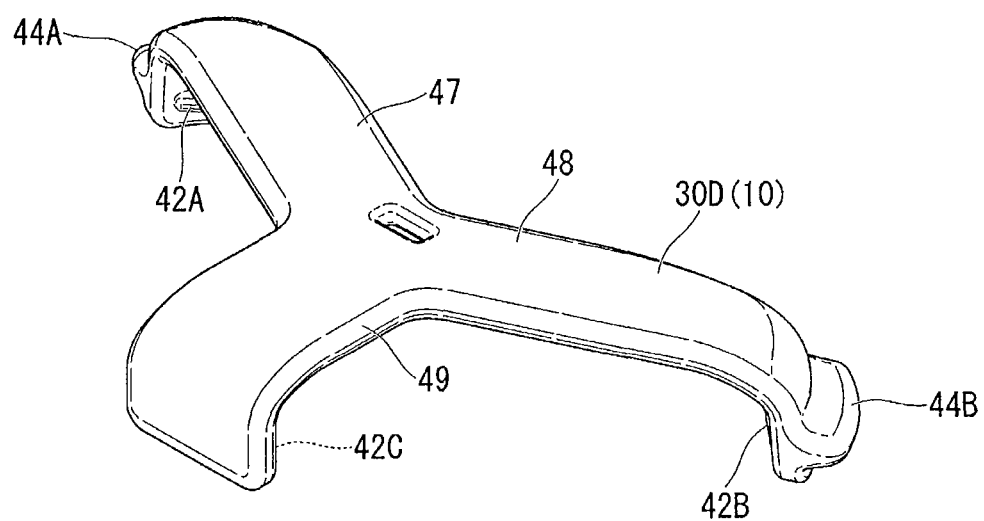
FIG. 15 is a perspective view of a fixing member included in the heart rate measuring device.
Figure 16:
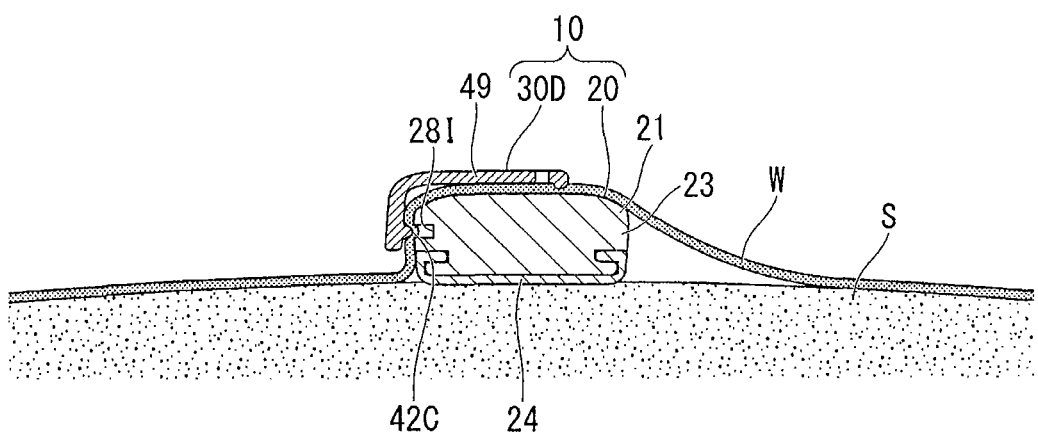
FIG. 16 is a cross-sectional view taken along Y-Y line of FIG. 14.

FIG. 14 is a front view showing a heart rate measuring device as a second modification example of the second embodiment of the present invention. FIG. 15 is a perspective view of a fixing member included in the heart rate measuring device. FIG. 16 is a cross-sectional view taken along Y-Y line of FIG. 14.

As shown in FIG. 14 to FIG. 16, a fixing member 30D has a Y-shape including a first band-shaped portion (corresponding to a "protective portion" in claims) 47 and a second band-shaped portion (corresponding to a "protective portion" in claims) 48 which extend from the center of the device body 20 toward two corner portions C1 and C2 which are adjacent along the longitudinal direction of the device body 20, and a third band-shaped portion (corresponding to a "protective portion" in claims) 49 extending toward an intermediate portion between remaining two corner portions C3 and C4 which are opposite to the corner portions C1 and C2 in the state where the fixing member 30D is attached to the device body 20.

Tip portions of the first band-shaped portion 47, the second band-shaped portion 48 and the third band-shaped portion 49 are curved toward one side with respect to a surface where the first band-shaped portion 47, the second band-shaped portion 48 and the third band-shaped portion 49 are positioned. In tip portions of the first band-shaped portion 47, the second band-shaped portion 48 and the third band-shaped portion 49, locking protrusions (corresponding to a "locking portion" in claims) 42A, 42B and 42C are respectively formed. In tip portions of the first band-shaped portion 47 and the second band-shaped portion 48, the protrusions 44A and 44B are respectively formed.

In the device body 20 side to be fixed to the garment W by the above fixing member 30D, concave portions 28G, 28H and 28I which are concave toward the inside of the case body 23 are formed at positions corresponding to the locking protrusions 42A, 42B and 42C as locked portions to which the fixing member 30D is locked.

Other Embodiments

The present invention is not limited to the above respective embodiments which have been explained with reference to the drawings, and various modification examples can be considered within a technical scope thereof.

For example, the concave portions 28A to 28I formed in the outer peripheral end surface 23f of the case body 23 in respective embodiments may be a groove continuously formed in the circumferential direction of the case body 23.

Also, the concave portions 28A to 28I formed in the outer peripheral end surface 23f of the case body 23 may not only be used for fixing the fixing members 30A to 30D but also used as, for example, holding portions for holding end portions of a belt for attaching the device body 20 to a chest, a wrist and so on of the user S.

In the above respective embodiments, the concave portions 28A to 28I are formed in the case body 23 side, and the locking portions 32A, 32B, the locking protrusions 42A to 42C are formed in the fixing members 30A to 30D side, however, the present invention is not limited to this. Accordingly, it is also preferable that, for example, convex portions or protruding ridges continuously formed in the circumferential direction are formed in the outer peripheral end surface 23f side of the case body 23 as locked portions, and concave portions or grooves are formed in the fixing members 30A to 30D side as locking portions.

Also in the above respective embodiments, the protrusions 44A and 44B for putting fingers are provided in the fixing members 30A to 30D, however, the shapes of the protrusions 44A and 44B are not limited to the above respective embodiments.

It is not always necessary to provide the protrusions 44A and 44B. However, when the protrusions 44A and 44B are provided, the fixing members 30A to 30D can be elastically deformed by putting fingers in the protrusions 44A and 44B as well as engagement between the device body 20 and each of the fixing members 30A to 30D can be easily released, therefore, the above respective embodiments are advantageous.

In the above respective embodiments, the so-called compression wear to be worn on an upper body of the user S has been explained as an example of the garment W, however, the present invention is not limited to this. Therefore, for example, a shirt other than the so-called compression wear to be worn on the upper body of the user S, pants to be worn on a lower body of the user S or a hat to be worn on a head of the user S can be used.

Also in the above embodiments, the device body 20 is arranged inside the garment W, and the device body 20 is fixed from the outside of the garment W by the fixing members 30A to 30D, however, the front side and the reverse side may be exchanged. That is, it is also preferable that the device body 20 is arranged outside the garment W, and the device body 20 is fixed from the inside of the garment W by the fixing members 30A to 30D.

Additionally, the structure of the device body 20 is not limited at all. For example, the outer shape of the device body 20 is not limited to the approximately rectangular shape but other various outer shapes such as various polygonal shapes, an elliptical shape and so on can be applied.

Furthermore, the electronic device is not limited to the heart rate measuring device 10 but electronic devices in various applications such as a music player, a camera, a telephone terminal, a wireless communication terminal, a passometer, and an ID (identification) tag, a GPS (global positioning system) device can be applied as portable electronic devices.

In the first embodiment, the fixing member 30A is formed in the oval shape in planar view, however, the shape of the fixing member 30A is not limited to the oval shape in planer view, and for example, a rectangular frame shape may be applied. That is, the fixing member 30A in the first embodiment is preferably formed so as to be elastically deformed as well as formed in a ring shape surrounding the device body 20.

It is possible to appropriately replace the components in the above embodiments with well-known components within a scope not departing from the gist of the present invention.

What is claimed is:

1. A portable electronic device configured to attach to a garment, the device comprising:
a device body configured to reside on one of a front side and a reverse side of the garment and housing an electronic component;
a fixing member separate from the device body and configured to reside on an opposite side from the front side and the reverse side of the garment, and configured to fix the device body so as to be attached and detached to and from the garment in a state of sandwiching the garment between the fixing member and the device body from the opposite side of the front side and the reverse side of the garment; and a pair of band-shaped electrode portions each having a first part extending into recessed regions of the device body and connected to the device body and having a second part extending away from the device body and configured to contact a biological surface; and a biological information detecting unit in the device body and configured to detect biological information based on a potential difference generated in the pair of electrode portions.

2. The portable electronic device according to claim 1, wherein the fixing member fixes an outer peripheral portion of the device body at least at two places.

3. The portable electronic device according to claim 1, wherein the device body includes a locked portion to which the fixing member is locked, and the fixing member comprises an elastically deformable material, and including a locking portion configured to lock to the locked portion.

4. The portable electronic device according to claim 1, wherein the fixing member comprises a ring shape surrounding the device body.

5. The portable electronic device according to claim 4, wherein a gap is defined at least in one side of the device body in a radial direction of the fixing member by an inner peripheral surface of the fixing member and the device body.

6. The portable electronic device according to claim 1, wherein the fixing member includes a protective portion configured to cover at least part of the device body through the garment from the opposite side of the front side and the reverse side of the garment.

\* \* \* \* \*